United States Patent [19]
Bek

[11] Patent Number: 5,785,831
[45] Date of Patent: Jul. 28, 1998

[54] MIXING LIQUIDS USING ELECTROOSMOTIC FLOW

[75] Inventor: Fritz Bek, Waldbronn, Germany

[73] Assignee: Hewlett-Packard Company, Palo Alto, Calif.

[21] Appl. No.: 598,717

[22] Filed: Feb. 8, 1996

[30] Foreign Application Priority Data

Feb. 19, 1995 [EP] European Pat. Off. ............ 95102304

[51] Int. Cl.$^6$ .......................... G01N 27/26; G01N 27/447
[52] U.S. Cl. ................................. 204/451; 204/601
[58] Field of Search ............................ 204/451, 452, 204/453, 454, 455, 456, 601, 602, 603, 604, 605

[56] References Cited

FOREIGN PATENT DOCUMENTS 4105107  9/1991  Germany .

OTHER PUBLICATIONS

Kurt Seiler et al, "Electroosmotic Pumping and Valveless Control of Fluid Flow within a Manifold of Capillaries on a Glass Chip" Analyical Chemistry, vol. 66, No. 20 (15 Oct. 1994) 3485–3491.

Stephen C. Jacobson et al "Microchip Capillary Electrophoresis with an Integrated Postcolumn Reactor" Analytical Chemistry, vol 66, No. 20 (15 Oct. 1994) 3472–3476.

European Search Report for Application No. 95102304.3 dated 11 Aug. 1995.

Analytical Chemistry, vol. 66, No. 20, 15 Oct. 1994 Columbus US, pp. 3485–3491, Seiler K et al "Electroosmotic pumping and valveless control of fluid flow within a manifold of capillaries on a glass chip" *whole document*.

Anayltical Chemistry, vol. 65, No. 10, 15 May 1993 Colombus US, pp. 1481–1488, Seiler K et al "Planar glass chips for capillary electrophoresis: repetitive sample injection, quantitation, and separation efficiency" *pg 1482, right column, para.2—p. 1848, right column, para.2; fig. 2*.

English Translation of Abstract from World Patent Index for DE–A–41 05 107 (Ciba–Geigy) (See item 1L) Oct. 1996.

Analytical Chemistry, vol. 66, No. 20, 15 Oct. 1994 Colombus US, pp. 3472–3476, Jacobson S C et al "Microchip capillary electrophoresis with an integrated postcolumn reactor" *pp. 3473, right column, para.3—pp. 3474, right column, para.1; fig. 1*.

Analytical Chemistry, vol. 66, No. 14, 15 Jul. 1994 Coloumbus US, pp. 2369–2373, Jacobson S C et al "Open channel electrochromatography on a microchip" *pp. 2371, left column, para.2—para.3; fig 1B*.

Primary Examiner—William H. Beisner
Assistant Examiner—John S. Starsiak, Jr.
Attorney, Agent, or Firm—Augustus W. Winfield

[57] ABSTRACT

A method and apparatus for mixing liquids using electroosmotic flow. Multiple capillaries (100, 104, 106) or microchip channels meet at a common junction (102). One capillary (100) is used for mixed liquids and each of the remaining capillaries (104, 106) are used for supplying a liquid (112, 114) to be mixed. Each of the supply capillaries (104, 106) has a free end that is immersed into a vial (108, 110) of liquid (112, 114). A first power supply terminal (112) is attached to a free end of the mixed liquid capillary (100). The liquid in each vial has an electrode that is switchably connected to a second power supply terminal. Closing a switch (116, 118) causes liquid to flow from a vial through the common junction and through the mixed liquid capillary. Each switch is independent and each may be closed continuously, switched at a constant duty cycle, or switched at a variable duty cycle. As a result, continuous mixing or variable ratio mixing may be achieved.

4 Claims, 1 Drawing Sheet

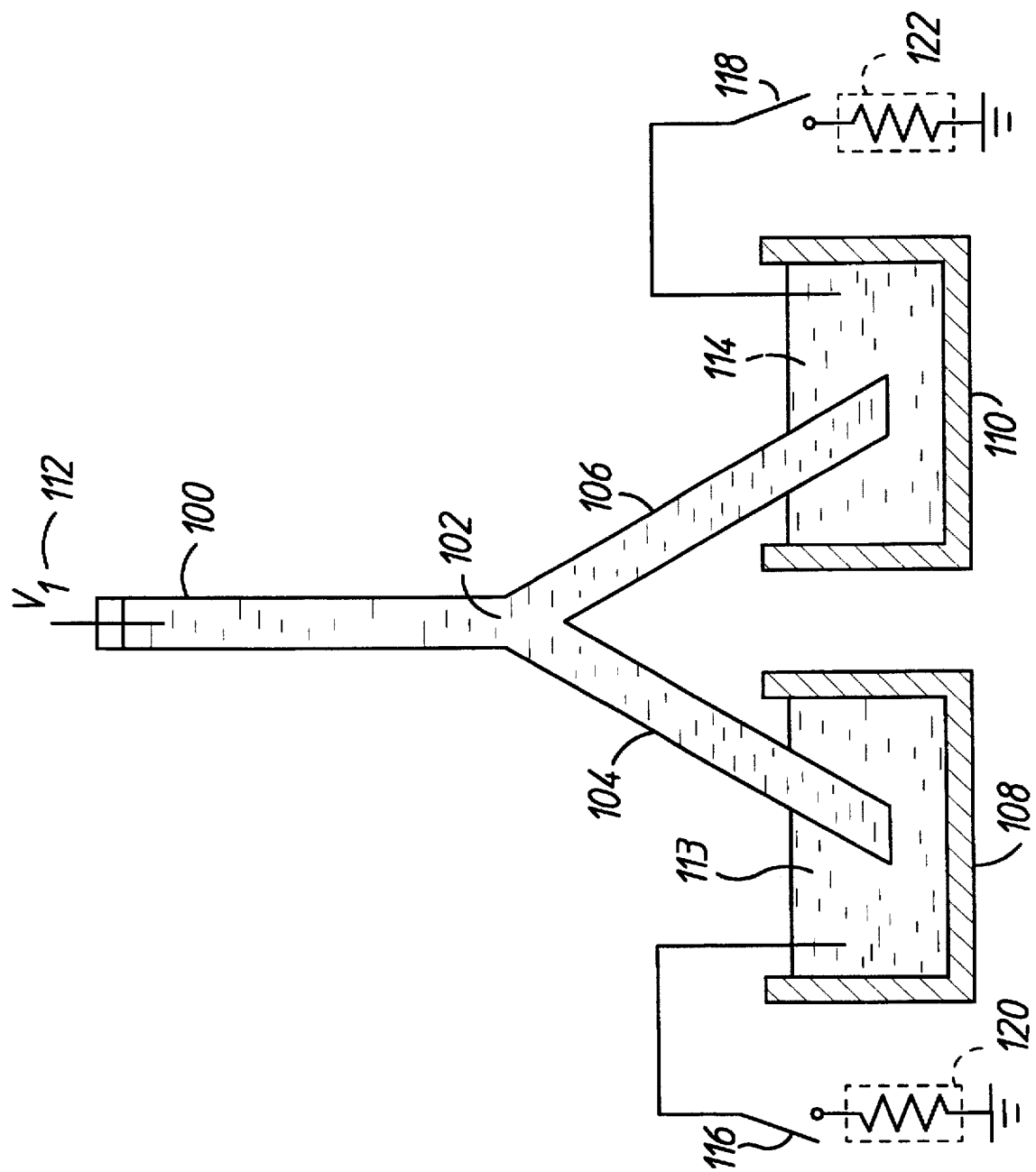

MIXING LIQUIDS USING ELECTROOSMOTIC FLOW

BACKGROUND OF THE INVENTION

1. Field of the Invention

This invention relates generally to instrumentation for analytical chemistry and more specifically to use of electroosmosis to mix liquids.

2. Description of the Prior Art

A common requirement in automated chemical separation systems is a precise continuous mix of multiple solvents or buffers. In particular, solvent mixtures are needed in liquid chromatography and in micellar electrophoresis. In liquid chromatography, it is useful to vary a solvent mix ratio over time. In some chemical separation systems, solvent mixtures are not common but would be useful if a low cost mixing system was available. In both liquid chromatography and capillary electrophoresis, there is a need for reduction in the size of the instrumentation in order to reduce the volume of samples needed for analysis and to make the instrumentation more portable. In addition, there is always a need to reduce cost and complexity. As an ultimate goal, there is interest in integrating electronics and chemical analysis onto a microchip, applying lithographic and etching techniques from the semiconductor fabrication industry to fabrication of channels for fluid flow in glass or semiconductor materials. In this application, specific embodiments of the invention will be described as using capillaries but the term capillary may be interchanged with the term microchip channel, where microchip channel in this context is a trench or trough suitable for fluid flow and fabricated on a microchip substrate.

Chromatographs typically use mechanical pumps for liquid propulsion. In addition, chromatography and electrophoresis analyzers typically use electromechanical valves for control of flow and mixing. In separation systems using tubes or capillaries packed with small particles, certain performance factors improve as the particle size decreases. However, small tubes and small particles require high pressure for liquid propulsion. In addition, microchip systems require very low flow rates, sometimes on the order of a few nl/min. Typically, mechanical pumps and valves have some finite stroke volume that limits their ability to achieve continuous low flow rates. In some systems, liquids are mixed at a high flow rate and then a fraction of the mixture is used with the remaining mixture wasted. As the size of the system decreases, the combined requirements for high pressure, low volume, and smooth continuous precision flow tend to make mechanical pumps and valves complex and expensive. Therefore, as the size of the system is reduced, there is a particular need for elimination of mechanical pumps and valves.

Electric fields can also be used for propulsion of a liquid. When a solid is immersed in a liquid, there may be some ionization of surface groups on the surface of the solid and some adsorption of ions present in the liquid, resulting in a net charge on the surface of the solid. The net charge on the surface of the solid attracts oppositely charged ions in the liquid, some of which remain in a mobile diffusion layer. When a tangential electric field is applied, the mobile ions migrate toward the appropriate electrode, carrying additional liquid along with them by viscous drag. Flow of a liquid in contact with a solid surface under the influence of a tangentially applied electric field is called electroosmosis (also sometimes called electroendosmosis).

Electroosmotic flow is particularly attractive in miniaturized analytical chemistry because it provides precise continuous flow with no moving mechanical parts. In addition, there are other benefits as follows. When hydrostatic pressure is used to move a liquid through a small open tube, surface tension at the wall of the tube impedes the flow of the liquid, resulting in a higher velocity flow in the center of the tube than at the wall of the tube. This non-uniform flow profile disperses the sample to be analyzed, decreasing the precision of the separation process. When hydrostatic pressure is used to move a liquid past small particles in a packed tube, shear forces at the surface of every particle impede flow, requiring high hydrostatic pressure to maintain flow rates. In contrast, in electroosmosis, the liquid flow is generated at a surface, resulting in a flat flow profile even in a very small diameter tube. In addition, particle surfaces also create mobile diffusion layers so that electroosmotic flow is not impeded by small particles, but instead is assisted. As a result, electroosmotic flow is particularly useful for pumping liquid through small tubes and tubes packed with small particles.

It has been proposed to use the term electrochromatography to designate any chemical separation technique using electroosmosis for liquid flow. For an overview of electrochromatography and electroosmotic flow, see for example, J. H. Knox, et al, "Miniaturization in Pressure and Electroendosmotically Driven Liquid Chromatography: Some Theoretical Considerations," Chromatographia, Vol. 24, 1987, pp. 135–143. For an example of electroosmosis used in flow injection analysis, see P. K. Dasgupta, et al, "Electroosmosis: A Reliable Fluid Propulsion System for Flow Injection Analysis," Analytical Chemistry, Vol. 66, No. 11, Jun. 1, 1994, pp. 1792–1798. For an example of research in the use of electroosmotic flow in microchips, see S. C. Jacobson, et al, "Open Channel Electrochromatography on a Microchip," Analytical Chemistry, Vol. 66, No. 14, Jul. 15, 1994, pp. 2369–2373. U.S. Pat. No. 4,140,121 (Kuhl et al) discloses use of electroosmotic flow in an implantable dosing device for releasing medication in a human or animal body. EPO application 0 616 218 A1 (Kamahori) discloses use of electroosmotic flow in a micro-reac None of the patents and articles disclosed above specifically addresses the problem of liquid mixing. Liquid mixing requires pumping and combining of multiple liquids, each at a different precise rate, and sometimes at precise time variable rates. In Kuhl et al, a single pre-mixed fluid is pumped. In Kamahori and in Dasgupta et al, electromechanical valves are used to control flow. In Jacobson et al, at any given time, either an analyte or a single buffer is pumped into a separation column with manual switching between the two. There is a need in electrochromatography and chemical microchip systems for liquid mixing systems having no moveable mechanical parts and in which multiple solvents or buffers are precisely mixed at low flow rates. In the case of electrochromatography, the mixing needs to occur before a sample is introduced and separation processes start.

SUMMARY OF THE INVENTION

An object of the invention is to provide a liquid mixing system using electroosmotic flow that is capable of precise continuous mixing at very low flow rates. A plurality of capillaries (or microchip channels) meet at a common junction. One capillary contains the mixed liquids and the remaining capillaries supply the liquids to be mixed. The mixed liquid is electrically connected to a first terminal of a power supply. Each of the supply capillaries has a free end that is immersed into a vial of liquid. The liquid in each vial is electrically connected to a second terminal of the power supply. The liquids may be connected directly to variable voltages, connected through variable resistors, or connected through switches. When an electrical circuit is completed through the power supply, the mixed liquid capillary, a supply capillary, and an associated vial of liquid, liquid flows by electroosmotic flow from the associated vial, through the associated supply capillary, to the common junction and into the mixed liquid capillary. Flow rates may be adjusted by adjusting the voltage for each liquid. Alternatively, flow rates may be adjusted by current limiting resistors. Alternatively flow rates can be adjusted by adjusting the duty cycle of switching and relative flow rates can be adjusted by adjusting the relative duty cycles of switching. A flow gradient (changing flow over time) can be generated for any particular liquid by varying the duty cycle of the associated switch over time.

BRIEF DESCRIPTION OF THE DRAWINGS

FIG. 1 is a block diagram illustration of a chemical mixing apparatus using electroosmotic flow in accordance with the invention.

DESCRIPTION OF THE PREFERRED EMBODIMENTS

FIG. 1 is a simplified block diagram illustrating an example embodiment of the invention. In FIG. 1, a capillary 100 is joined to at least two other capillaries (104 and 106) at a common point 102. The free end of capillary 104 is immersed into a first liquid in a first vial 108. The free end of capillary 106 is immersed into a second liquid in a second vial 110. Liquid in capillary 100 is connected through the free end of capillary 100 to a voltage $V_1$ (112). The liquid 113 in vial 108 is switchably connected to ground by switch 116. The liquid 114 in vial 110 is switchably connected to ground by switch 118. Each capillary is filled with liquid.

Assuming that the material in the capillary walls can create a suitable surface charge, that the voltage 112 has the proper polarity and has sufficient magnitude to generate a current through the capillaries, and that the liquids in the two vials contain some ions, then when switch 116 is closed, liquid is pumped by electroosmosis from vial 108 toward the free end of capillary 100 and when switch 118 is closed, liquid is pumped by electroosmosis from vial 110 toward the free end of capillary 100. If both switches are closed, liquid is pumped from both vials simultaneously, continuously mixing at junction 102.

In general, with a fixed voltage, liquids having different ion concentrations will flow at different rates. For continuous mixing, the switches can be closed continuously and rates can be controlled by use of series resistors (120, 122) to limit current flow. Alternatively, different voltages can be provided to each liquid so that the flow rate is determined by voltage. Preferably, for simplicity, a single voltage is used as illustrated and the resistors are not present (switches 116 and 118 switch directly to ground) and flow is adjusted by controlling switching duty cycle. The two switches are independent, It is not necessary for switches 116 and 118 to be synchronized. In addition, it is not necessary for switches 116 and 118 to be switched at the same frequency. However, proper mixing is partially frequency dependent. For each liquid, average flow rate is determined by the duty cycle of the associated switch. If the switching frequency has a period that is long compared to the response time of the liquid and the electroosmotic pumping, then liquid is pumped in discrete packets. If switches 116 and 118 are alternately closed at a very low frequency, liquid is alternately pumped from each vial, generating sequential packets of liquid in capillary 100. If the frequency is too low, sequential packets may not completely mix. If the switching frequency becomes high enough, then the packets become so small that even if the packets alternate, liquid from each vial is mixed at the junction 102 by diffusion, producing a substantially uniform composition of liquids. At a still higher frequency, the voltage changes faster than the liquid and electroosmotic pumping can respond and the flow is essentially continuous and controlled by the average value of the switched voltage. A typical range of frequencies suitable for mixing is in the range of 10–100 Hz. Overall flow rate can be adjusted by adjusting the duty cycle of both switches equally. The relative flow rates from vials 108 and 110 can be adjusted by adjusting the relative duty cycle of switches 116 and 118. In addition, the flow rate of one liquid can be varied over time (for example, for a programmed solvent gradient) by varying the duty cycle of the corresponding switch over time.

For each liquid in FIG. 1, the flow rate is affected by the height of the liquid in the vial. That is, the electroosmotic pump must pump against the gravity induced hydrostatic pressure (head) of the liquid. Therefore, flow rate may vary over time as a vial is emptied. In addition, when a particular switch is open and no electroosmotic pumping pressure is generated, the liquid in the corresponding capillary may flow back into the corresponding vial. With very small capillaries (less than 100 micrometer in diameter), the effects of liquid head are negligible because the electroosmotic pumping is high relative to the liquid head and the effects of back flow are negligible because viscous friction at the capillary wall resists back flow.

As discussed in the background section above, small particles provide additional charged surfaces. As a result, small particles increase the effective pressure of electroosmotic flow because of the increased pumping effect of the additional charged surfaces on the particles. Therefore, if capillaries 104 and 106 are packed with small particles, then the hydrostatic effects of liquid height become negligible relative to the electroosmotic pumping pressure. In addition, as discussed in the background section above, small particles tend to resist flow generated by hydrostatic pressure. As a result, if capillaries 104 and 106 are packed with small particles, then backflow during off cycles is reduced. Therefore, with larger capillaries (greater than 100 micrometers diameter), capillaries 104 and 106 are preferably packed with small particles. Of course, liquid levels in vials can be measured or flow rates can be measured and closed loop systems provided but packed capillaries are simple, low cost and effective.

Capillary 100 may supply a solvent mixture to a separate electrochromatography system, or capillary 100 may be the separation capillary for an electrophoresis system (for example micellar electrophoresis), or capillary 100 may be a separation column for chromatography (electrochromatography using electroosmosis for liquid flow instead of hydrostatic pressure). If capillary 100 is a separation capillary or column, then a sample (analyte) must also be introduced at junction 102. The sample can also be injected by electroosmotic flow (see for example, Jacobson et al), or by gravity flow or other hydrostatic pressure (for example, by syringe). In general, more than two capillaries may be joined at the common junction and one of those capillaries may be for a sample rather than for a solvent. If a packed capillary is used for sample injection, then some separation may occur in the loading capillary instead of the separation capillary 100. Preferably, a detachable connection is used between capillary 100 and junction 102. Then it is possible to inject directly into capillary 100.

In general, liquids capable of electroosmotic pumping must have some minimum ion concentration. In electrochromatography, suitable liquids include buffers and organic solvents premixed with water (for example, 10% water). Silica surfaces, common in capillaries and microchips, bear fixed negative charges, resulting in a boundary layer in the liquid solution containing an excess of positively charged ions. The positively charged ions move toward a negative electrode. A typical required field strength is 50,000 V/m. The magnitude of the electric current is typically in the range of 1-100 microamps. Some heating occurs, given by $V^2/R$, where V is the voltage across the capillary and R is the resistance of the capillary. With a packed capillary, a small diameter capillary is preferable to avoid diffusion effects of temperature gradients. Electrodes are preferably a non-reactive metal such as platinum or gold.

In a specific example embodiment used to demonstrate mixing, capillaries 100, 102 and 104 have a diameter of 50 micrometers and are open. The voltage 112 is negative 20 kV. Vial 1 (108) contains sodium phosphate buffer with pH 6.5 and switch 116 is continuously closed. Vial 2 (110) contains buffer mixed with DMSO for detection in an absorbance spectrometer. Switch 118 is switched at a frequency of 10 Hz with a duty cycle ranging from 10% to 90%. The average current flow is approximately 18 microamps. The average fluid flow rate is approximately 23 nl/min. One percent changes in duty cycle are detectable by the absorbance spectrometer.

What is claimed is:

1. A method of mixing liquids, the method comprising the following steps:

(a) pumping a first liquid by electroosmosis into a junction, with a pumping voltage switched by a first switch;

(b) pumping a second liquid by electrosmosis into the junction, with a pumping voltage switched by a second switch; and, (c) switching at least one of the first and second switches on and off at a frequency that is sufficiently high-to produce a substantially uniform composition of the first liquid and the second liquid at the junction.

2. The method of claim 1, the switching in step (c) switched on and off at a constant duty cycle.

3. The method of claim 1, the switching in step (c) switched on and off at a variable duty cycle.

4. An apparatus for mixing liquids, the apparatus comprising:

a first capillary or microchip channel having first and second ends, the first end of the first capillary or microchip channel immersed in a first liquid;

a second capillary or microchip channel having first and second ends, the first end of the second capillary or microchip channel immersed in a second liquid;

the second end of the first capillary or microchip channel and the second end of the second capillary or microchip channel connected at a junction;

a power supply providing a voltage between the first liquid and the junction and between the second liquid and the junction;

a first resistor connected so as to limit current from the power supply through the first liquid;

a second resistor connected so as to limit current from the power supply through the second liquid;

the first and second liquids flowing into the junction by electroosmosis to form a substantially uniform composition of the first and second liquids at the junction; and the flow rate of the first liquid dependent on the first resistor and the flow rate of the second liquid dependent on the second resistor.

* * * * *